United States Patent [19]  
Gosteli

[11] 4,206,152  
[45] Jun. 3, 1980

[54] PROCESS FOR THE PRODUCTION OF UNSUBSTITUTED OR POLYSUBSTITUTED O-PHTHALALDEHYDES

[75] Inventor: Jacques Gosteli, Basel, Switzerland

[73] Assignee: Ciba-Geigy Corporation, Ardsley, N.Y.

[21] Appl. No.: 971,772

[22] Filed: Dec. 21, 1978

[30] Foreign Application Priority Data

Dec. 30, 1977 [CH] Switzerland ..................... 16298/77  
Apr. 4, 1978 [CH] Switzerland ......................... 3601/78

[51] Int. Cl.² .............................................. C07C 45/00  
[52] U.S. Cl. ................................. 568/435; 260/465 R; 260/465 H; 562/459; 568/424; 568/436

[58] Field of Search ............... 260/599, 600 R, 465 R, 260/465 H; 562/459

[56] References Cited

U.S. PATENT DOCUMENTS

| 4,079,075 | 3/1978 | Lee et al. .......................... 260/599 X |
| 4,125,561 | 11/1978 | Redecker et al. ..................... 260/599 |

*Primary Examiner*—Bernard Helfin  
*Attorney, Agent, or Firm*—John J. Maitner

[57] ABSTRACT

The present invention provides a process for the production of unsubstituted or substituted o-phthalaldehydes by hydrolysis of $\alpha,\alpha, \alpha',\alpha'$-tetrahalogeno-o-xylenes with a carboxylate in an aqueous medium in the presence of a phase transfer catalyst and an organic base.

5 Claims, No Drawings

PROCESS FOR THE PRODUCTION OF UNSUBSTITUTED OR POLYSUBSTITUTED O-PHTHALALDEHYDES

A number of different processes for the production of o-phthalaldehyde have long been described in the literature. One such process is the multi-step oxidation method of J. Thiele and E. Winter, A 311, 360 (1900), which starts from o-xylene and proceeds via the phthalaldehyde tetraacetate. The method described by F. Weygand and D. Tietjen in B 84, 625 (1951), wherein N,N,N′N′-tetramethyl-o-phthalamide as suitable carboxylic acid derivative is reduced with lithium aluminium hydride, yields o-phthalaldehyde. Reduction of the tetramethyl-o-phthalamide can only be carried out with the most rigorous exclusion of moisture, so that considerable technical problems have to be reckoned with. A further process described by F. Wygand, K. G. Kinkel and D. Tietjen in B 83, 394 (1950) starts from o-phthalalcohol. The alcohol is oxidised with selenium dioxide, affording the ester of selenious acid as intermediate, which is converted to the aldehyde only by cautious heating over an open flame. An interesting method hitherto has been the hydrolysis of α,α,α′,α′-tetrabromo-o-xylene with potassium oxalate described by J. Thiele and O. Günther, A 347, 106 (1906). A drawback of this process was the lengthy reaction time and the absolutely essential use of a solvent mixture of alcohol and water in relatively large volumetric amounts. The hydrolysis of tetrabromo-o-xylene described by F. Weygand et al., B 80, 391 (1947), can also be accounted an interesting method. The drawback here, however, is the use of fuming sulfuric acid. The large volume of aqueous sulfuric acid solution obtained by pouring the reaction mixture on ice has to be saturated with large amounts of sodium chloride and extracted with substantial volumetric amounts of ethyl acetate. Although o-phthalaldehyde has long been ranked among the known substances, there is still at the present time no simple synthesis, i.e. one using inexpensive starting materials and reagents and requiring few steps, for the production of this compound in good yield.

Accordingly, the present invention provides a particularly advantageous process for the production of unsubstituted or substituted o-phthaladehydes.

The process of the present invention for the production of an unsubstituted or substituted o-phthalaldehyde of the formula I

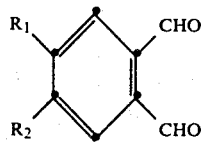

wherein $R_1$ and $R_2$, each independently of the other, represent hydrogen, lower alkyl, hydroxyl, halogen, nitro, cyano or carboxyl, consists in hydrolysing an unsubstituted or substituted α,α,α′,α′-tetrahalogeno-o-xylene of the formula II

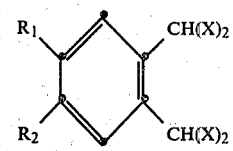

wherein $R_1$ and $R_2$ are as defined for formula (I) and X represents a halogen atom, with a carboxylate in an aqueous medium in the presence of a phase transfer catalyst and an inorganic base.

$R_1$ and/or $R_2$ as lower alkyl can be a straight chain or branched lower alkyl radical of 1 to 7 carbon atoms, for example preferably methyl, ethyl, n-propyl and isopropyl, and also n-butyl, isobutyl, sec-butyl, tert-butyl, n-amyl, isoamyl, n-hexyl, isohexyl or n-heptyl.

Suitable halogen atoms represented by $R_1$ and $R_2$ are those with an atomic number up to 35, for example fluorine, chlorine or bromine. The preferred substituent X of the starting compound of the formula (II) is chlorine or bromine.

By carboxylate is meant the salt of an organic carboxylic acid. Suitable salts are in particular metal salts, such as alkali metal or alkaline earth metal salts, and also ammonium salts, of such acids, especially of corresponding aliphatic and also aromatic carboxylic acids, such as lower alkanoic acids, for example formic, acetic or propionic acid, as well as benzoic acid. Preferably, an alkali metal lower alkanoate is employed, such as sodium or potassium alkanoate, and also calcium alkanoates of 1 to 3 carbon atoms, including the formiates, especially the corresponding formiates and acetates and, in particular, sodium or potassium formiate or sodium or potassium acetate.

Preferred phase transfer catalysts are onium salts, in particular quaternary ammonium salts and phosphonium salts, for example tetraalkylammonium and tetraalkylphosphonium salts, especially corresponding halides, such as tetra-n-butylammonium chloride or bromide and tetra-n-butyl-phosphonium chloride or bromide, ethyl trioctylphosphonium chloride or bromide or aryl-lower alkyl-tri-lower alkyl ammonium salts, in particular corresponding halides, for example benzyltriethylammonium chloride. In analogous manner, it is also possible to use the corresponding arsonium and sulfonium salts (E. V. Dehmlow, Ang. Chem. 89/8, 521–533).

To neutralise the acid which forms during the hydrolysis of acylal intermediates and which corresponds to the carboxylate reagent, and to speed up this hydrolysis, a base is added. An inorganic base is ordinarily employed, such as a corresponding metal base, for example an alkali metal or alkaline earth metal base, especially a corresponding hydroxide, hydrogen carbonate or preferably carbonate, such as sodium or potassium hydroxide or sodium or potassium hydrogen carbonate, and preferably potassium carbonate or, most preferably, sodium carbonate. In analogous manner, it is possible to use a corresponding hydroxide, hydrogen carbonate and carbonate of calcium or magnesium. If desired, calcium carbonate may be preferred as sparingly soluble base.

The reaction is ordinarily carried out in a two-phase system consisting of an aqueous phase and an organic phase, the latter being formed of the α,α,α′,α′-tetrahalogeno-o-xylene, for example from the α,α,α′,α′- tetrabromo-o-xylene or α,α,α',α'-tetrachloro-o-xylene. The amounts of carboxylate and phase transfer catalyst compounds to be used according to the invention can vary greatly. An inorganic base is added to the reaction mixture to neutralise the resulting acid, which converts this again into the carboxylate compound. It would be possible to use theoretically catalytic amounts, i.e. less than equimolar amounts, for example from about 1 mol.% to about 50 mol.% (based on the starting material), of both the carboxylate and of the phase transfer compound. The latter is ordinarily added in catalytic amounts, for example from about 1 mol.% to about 30 mol.% (based on the starting material), whilst equimolar amounts or an excess of the phase transfer catalyst can also be used. Approximately equimolar amounts of the carboxylate compound are usually employed: if appropriate, a less than equivalent amount and preferably an excess is employed. A readily soluble base, such as an alkali metal carbonate, for example sodium carbonate, is preferably added in the course of the reaction, usually in portions. If necessary, the reaction mixture is cooled temporarily before the addition of the base, for example to prevent foaming when using a carbonate or hydrogen carbonate. However, a sparingly soluble base can also be present from the start in the reaction mixture, for which reason it is also preferred to use such a base, for example calcium carbonate.

When using a readily soluble base, for example an alkali metal base, the hydrolysis is preferably carried out in a pH range from about 7.5 to about 11, and in the presence of a sparingly soluble base, for example an alkaline earth metal carbonate, for example calcium carbonate, it is carried out in a pH range below 7.5; depending on the solubility of the alkali earth metal carbonate, the pH value falls to about 4.

As the α,α,α',α'-tetrabromo-o-xylene or α,α,α',α'-tetrachloro-o-xylene, as starting material in the fused state, forms the orgaic phase of the two-phase system, the reaction is preferably carried out at a temperature above 60° C., for example at a temperature from about 60° C. to about 160° C., preferably from 90° C. to about 140° C., and also under normal pressure or elevated pressure, for example in a bomb tube or an autoclave, and/or in an inert gas atmosphere, for example nitrogen or argon.

The unsubstituted or substituted α,α,α',α'-tetrabromo-o-xylene or α,α,α'-α'-tetrachloro-o-xylene used as starting material are known compounds and can be obtained, for example, by treatment of an o-xylene with elementary bromine under irradiation with UV light (Organic Syntheses, Coll. Vol. IV, pp. 807-808) or by treatment of an o-xylene with elementary chlorine under irradiation with visible light (Houben-Weyl, Vol. 5/3, page 739).

In comparison with the closest prior art, i.e. compared with the process described by F. Weygand et al., B 80, 391 (1947), the hydrolysis is carried out without fuming sulfuric acid. The large amount of aqueous solution, which is saturated with sodium chloride, occurring in this prior art process must in turn be extracted with a large volume of ethyl acetate as solvent. These drawbacks do not arise in the process of the present invention.

The unsubstituted or substituted o-phthaladehydes obtained by the process of the present invention are used, for example, as reagents for the qualitative and quantitative determination of ammonia or also of primary amines (in peptide chemistry). Secondary amines do not react with o-phthalaldehyde.

The invention is illustrated by the following Examples.

EXAMPLES

EXAMPLE 1

With efficient stirring, a suspension consisting of 10 g (23.7 mmols) of α,α,α',α'-tetrabromo-o-xylene, 9.7 g (118 mmols) of sodium acetate, 1.74 g (5.4 mmols) of tetrabutylammonium bromide, 4.75 g of calcium carbonate and 10 ml of distilled water is heated to reflux in a nitrogen atmosphere, whereupon the temperature rises to 118° C. After a reaction time of 6 hours, the reaction mixture is cooled and, after the addition of 50 ml of ethyl acetate, filtered. The organic phase is separated in a separating funnel and the aqueous phase is washed once more with ethyl acetate. The combined organic extracts (ethyl acetate extracts) are washed with a solution of sodium chloride, dried over magnesium sulfate and then concentrated in vacuo. The residue is taken up in 40 ml of toluene and the solution is purified by chromatography through a column packed with 100 g of silica gel. After elution with toluene, concentration of the eluate yields 2.10 g (66.2% of theory) of o-phthalaldehyde with a melting point of 53°-55° C.

EXAMPLE 2

With efficient stirring, a suspension consisting of 10 g of α,α,α',α'-tetrabromo-o-xylene, 8 g of sodium formiate, 1.74 g of tetrabutyl ammonium bromide, 4.75 g of calcium carbonate and 10 ml of distilled water is refluxed for 9 hours in a nitrogen atmosphere. After cooling, 50 ml of ethyl acetate are added to the reaction mixture, which is further worked up as in Example 1. Yield: 2.54 g (80.2% of theory) of o-phthalaldehyde with a melting point of 53°-55° C. after purification by chromatography through a column of silica gel (100 g).

EXAMPLE 3

In accordance with Example 1, a suspension consisting of 5.78 of α,α,α',α'-tetrachloroxylene (purity approx. 95%), 9.62 g of sodium acetate, 1.74 g of tetrabutylammonium bromide, 4.75 g of calcium carbonate and 10 ml of water is refluxed, with stirring, for 29 hours in a nitrogen atmosphere. After cooling, the reaction mixture is diluted with water and extracted with two 100 ml portions of ethyl acetate. The combined organic layers are washed with a saturated solution of sodium chloride and dried over magnesium sulfate. The solvent is distilled off in vacuo and the crystalline residue is dissolved in toluene and chromatographed through 100 g of silica gel. o-Phthalaldehyde is eluted with toluene/ethyl acetate (19:1) and the eluate is concentrated, affording 2.30 g (72%) of pure o-phthalaldehyde.

What is claimed is:

1. A process for the production of an unsubstituted or substituted o-phthalaldehyde of the formula I

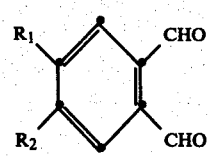
(I)

wherein $R_1$ and $R_2$, each independently of the other, represent hydrogen, lower alkyl, hydroxyl, halogen, nitro, cyano or carboxyl, which comprises hydrolysing at a pH-range between 4-11 an unsubstituted or substituted $\alpha,\alpha,\alpha',\alpha'$-tetrahalogeno-o-xylene of the formula II

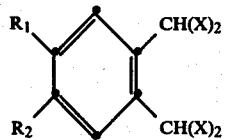
(II)

wherein $R_1$ and $R_2$ are as defined for formula (I) and X represents a halogen atom, with an alkali metal salt, alkaline earth metal salt or ammonium salt of a lower alkanecarboxylic acid or of an aromatic carboxylic acid in the presence of an optionally substituted tetra lower alkyl ammonium as phase transfer catalyst and of an alkali metal carbonate or alkaline earth metal carbonate at a temperature above 60° C.

2. A process according to claim 1 wherein the hydrolysis is carried out in the presence of tetra-n-butylammonium chloride or tetra-n-butylammonium bromide as phase transfer catalyst, and of an alkali metal carbonate or alkaline earth metal carbonate, with an alkali metal formate or acetate or an alkaline earth metal formate or acetate.

3. A process according to claim 1 wherein the hydrolysis is carried out in the presence of benzyltriethylammonium chloride or bromide and of an alkali metal carbonate or alkaline earth metal carbonate, with an alkali metal formate or acetate or alkaline earth metal formate or acetate.

4. A process according to claim 1 wherein the hydrolysis is carried out in the presence of tetra-n-butylammonium chloride or bromide and of calcium carbonate, with sodium formate or acetate.

5. A process according to claim 1 wherein the unsubstituted or substituted $\alpha,\alpha,\alpha',\alpha'$-tetrahalogeno-o-xylene of the formula II is an unsubstituted or substituted $\alpha,\alpha,\alpha',\alpha'$-tetrabromo-o-xylene or $\alpha,\alpha,\alpha',\alpha'$-tetrachloro-o-xylene.

* * * * *